United States Patent [19]

Tward

[11] Patent Number: 4,468,611

[45] Date of Patent: Aug. 28, 1984

[54] CAPACITIVE SYSTEM FOR MONITORING THE DIELECTRIC PROPERTIES OF FLOWING FLUID STREAMS

[75] Inventor: Emanuel Tward, Northridge, Calif.

[73] Assignee: Tward 2001 Limited, Los Angeles, Calif.

[21] Appl. No.: 383,792

[22] Filed: Jun. 1, 1982

[51] Int. Cl.³ ............................................. G01R 27/26
[52] U.S. Cl. ............................. 324/61 R; 324/DIG. 1
[58] Field of Search ........................ 324/61 R, DIG. 1; 73/61 R, 61.1 R

[56] References Cited

U.S. PATENT DOCUMENTS

| | | | |
|---|---|---|---|
| 2,485,579 | 10/1949 | Elliott | 324/61 R |
| 2,594,138 | 4/1952 | Elam | 324/61 R X |
| 2,599,583 | 6/1952 | Robinson et al. | 324/61 R |
| 2,800,628 | 7/1957 | Stinson et al. | 324/61 R |
| 3,123,751 | 3/1964 | Balsbaugh | 324/61 R X |
| 3,238,452 | 3/1966 | Schmitt et al. | 324/61 R |
| 3,279,249 | 10/1966 | Tocanne | 324/61 R X |
| 3,421,077 | 1/1969 | Liu et al. | 324/61 R |
| 3,665,300 | 5/1972 | Sauer et al. | 324/61 R |
| 3,675,121 | 7/1972 | Thompson | 324/61 R |
| 4,266,188 | 5/1981 | Thompson | 324/61 R |

Primary Examiner—Stanley T. Krawczewicz
Attorney, Agent, or Firm—Philip D. Junkins

[57] ABSTRACT

A method and instrument for comparing the dielectric properties of a flowing stream of fluid with the dielectric properties of a reference fluid in which a uniquely configured multi-capacitor sensor, formed of a first pair of capacitors having like dielectric spaces within which the reference fluid is maintained under non-flow conditions as the dielectric material and a second pair of capacitors having like dielectric spaces within which a sample portion of the flowing stream of fluid is continuously passed as the dielectric material, comprises all of the capacitance elements of a Wheatstone bridge circuit in a single cellular unit in which the capacitive elements are all subjected to the same sample fluid, temperature and pressure environment and which is not sensitive to stray capacitances. Each pair of capacitors forms opposing sides of the Wheatstone bridge circuit. A source of alternating current of constant voltage and set frequency is applied across a first set of bridge terminals at opposite corners of the bridge and a current detection circuit is connected across a second set of bridge terminals independent of the first set of terminals and at opposite corners of the bridge. Detection and measurement of the current value of the bridge is translated into a value of dielectric constant for the fluid sample in direct linear relationship with the current value.

19 Claims, 8 Drawing Figures

CAPACITIVE SYSTEM FOR MONITORING THE DIELECTRIC PROPERTIES OF FLOWING FLUID STREAMS

BACKGROUND OF THE INVENTION

1. Field of the Invention

The present invention pertains to a novel system for monitoring various properties of flowing fluid streams and more particularly relates to an instrument and a method, using a multiplicity of electrical capacitors in a capacitance measuring bridge circuit, for the continuous inspection and monitoring of flowing fluid streams and comparing the dielectric properties of such streams with a reference fluid.

2. Description of the Prior Art

Many techniques have been suggested and developed to sample flowing fluid streams and compare stream samples with a reference fluid. In the prior art it is common to provide apparatus for measuring the conductivity of liquids, such as oils and the like, to determine the amount of impurities therein. If the impurities in the liquid have a different conductivity than that of the liquid, the conductivity of the combination of liquid and impurity will be altered with respect to the conductivity of the pure liquid and the difference in conductivities can be measured and reported. However, many impurities associated with or introduced into flowing liquid streams do not alter the conductivity of the liquid and thus may not be detected by flow monitoring instruments measuring conductivity changes.

It has been suggested in a number of prior art patents and patent applications to monitor and inspect the flow of fluids in product pipe lines, particularly petroleum products, by the passage of a sample stream of the fluid through a cell which is connected in a circuit energized by constant and relatively high frequency alternating potential under conditions wherein the fluid sample stream functions as a dielectric medium for the cell. The character of the fluid is then detected as a function of the dielectric constant of the sample stream as it passes through the cell by measuring the potential developed across the cell. It has been found that, in carrying out dielectric constant detection methods for monitoring and inspecting the character of flowing fluids, changes in temperature and pressure affect the dielectric constant of the sample stream flowing through the cell.

To overcome the adverse effects of changes of temperature and pressure on the dielectric constant of samples of flowing fluids, instruments have been designed to include dual capacitor cells which are connected in a capacitance bridge circuit including a sensing cell through which the sample stream is passed and a reference cell which contains a fluid having a known desired dielectric constant against which the dielectric constant of the sample stream is compared. By maintaining the two cells in intimate thermal contact with the sample stream, and by equalizing the pressure therebetween, changes in the dielectric constant of the sampled fluid due to temperature or pressure variations, which otherwise might promote spurious results and erroneously cause recording equipment to indicate a change of constitution of the sampled stream, can be compensated for to some extent. An instrument designed in accordance with the foregoing has been disclosed in U.S. Pat. No. 2,800,628 granted to L. W. Stinson et al on July 23, 1957.

Reference to the Stinson et al patent will reveal that the two capacitor cells of the instrument are each comprised of a single capacitor and that such capacitors are connected as the two variable capacitors in classic capacitive Wheatstone bridge circuitry. The remaining two capacitors of the Wheatstone bridge (fixed impedance value) are removed from the environment (fluid characteristics, pressure and temperature) of the two capacitor cells of the instrument. Thus, the entire bridge circuitry remains sensitive to temperature and pressure differences. Also, long lead lengths and moving leads allow stray capacitance pickup and overall variations in circuit impedence.

SUMMARY OF THE INVENTION

The present invention relates to an instrument and a method for continuously inspecting and monitoring flowing fluid streams and comparing the dielectric properties of such streams with a reference fluid. The invention overcomes the deficiencies of prior art capacitive methods and instrumentation by uniquely combining all of the capacitances involved in the dielectric monitoring and dielectric comparison circuitry in a single cellular unit in which the capacitance elements are all subjected to the same sample fluid, temperature and pressure environment and which is not sensitive to stray capacitances.

It is an object of the present invention to provide an improved capacitive method and instrumentation for monitoring the dielectric properties of flowing fluid streams.

It is a further object of the present invention to provide an improved capacitive type fluid test instrument which can accurately measure chemical or structural changes in a wide variety of fluids.

It is another object of the present invention to provide an improved capacitive type method for testing the properties of flowing fluid streams which is insensitive to environmental changes and to stray capacitances.

It is a still further object of the present invention to provide an improved dielectric sensitive instrument for receiving sample fluid from a flowing fluid stream and monitoring such fluid to accurately measure and compare the dielectric constant of such fluid with a reference fluid.

Another object of the present invention is to provide an improved capacitive type fluid sensing method for monitoring the dielectric properties of flowing fluids, utilizing a multi-capacitor sensor cell containing all of the capacitors of a simple alternating current Wheatstone bridge circuit and including detector and direct readout circuitry, which is insensitive to changes in the environmental characteristics of the flowing fluid or to stray capacitance in the presence of the sensorbridge system.

These and other objects of the invention will become apparent to those skilled in the art upon consideration of the accompanying specification, claims and drawings.

BRIEF DESCRIPTION OF THE DRAWINGS

Referring to the drawings, wherein like characters indicate like parts throughout the figures.

DESCRIPTION OF THE PREFERRED EMBODIMENTS

The present invention is intended as an improvement to conventional capacitance type flowing fluid monitoring methods and instrumentation and is broadly suitable for use in the monitoring of various properties of flowing fluid streams. The method and instrumentation are broadly suitable for use with respect to electrical conducting and non-conducting fluids which are comprised, at least in part, of a liquid material.

It is to be noted and understood that, throughout this specification and the appended claims, the term or word "fluid" shall and does mean a uni-component or multi-component liquid composition which may exhibit electrically non-conducting or electrically conducting characteristics. Thus, the term "fluid" encompasses (without limitation) a wide variety of: liquids, liquid/liquid mixtures or emulsions, liquid/gas mixtures or dispersions, and liquid/solid mixtures. In further definition of the term "fluid," it is to be understood that multi-component substances comprising a fluid must exhibit for each component a different and determinable dielectric value. Thus, for multi-component fluids or fluids comprised of different phases of the same substances, measurable differences must be exhibited with respect to the dielectric constants for such components or phases.

For purposes of ease of description of the invention and its application to fluid monitoring, the method and instrumentation comprising the invention will, for the most part, be discussed in terms of their applicability to monitoring and comparing of the dielectric properties of liquid process streams such as hydrocarbons flowing in a petroleum products pipe line.

The fluid monitoring method and instrumentation of the invention utilizes a uniquely configured arrangement of four plate type capacitors extending in clustered parallel alignment throughout substantially the full length of the monitoring instrument. The four capacitors are constructed from four electrically conductive capacitor elements each comprised of two electrically connected capacitive plates. The capacitor elements are mounted in fixed, equally spaced relationship from one another and positioned by the monitor body and associated mounting means so that each plate of each capacitor element defines with a plate of the next adjacent capacitor element a dielectric space therebetween whereby the mounted capacitor elements together form four dielectric spaces.

Figure 1:
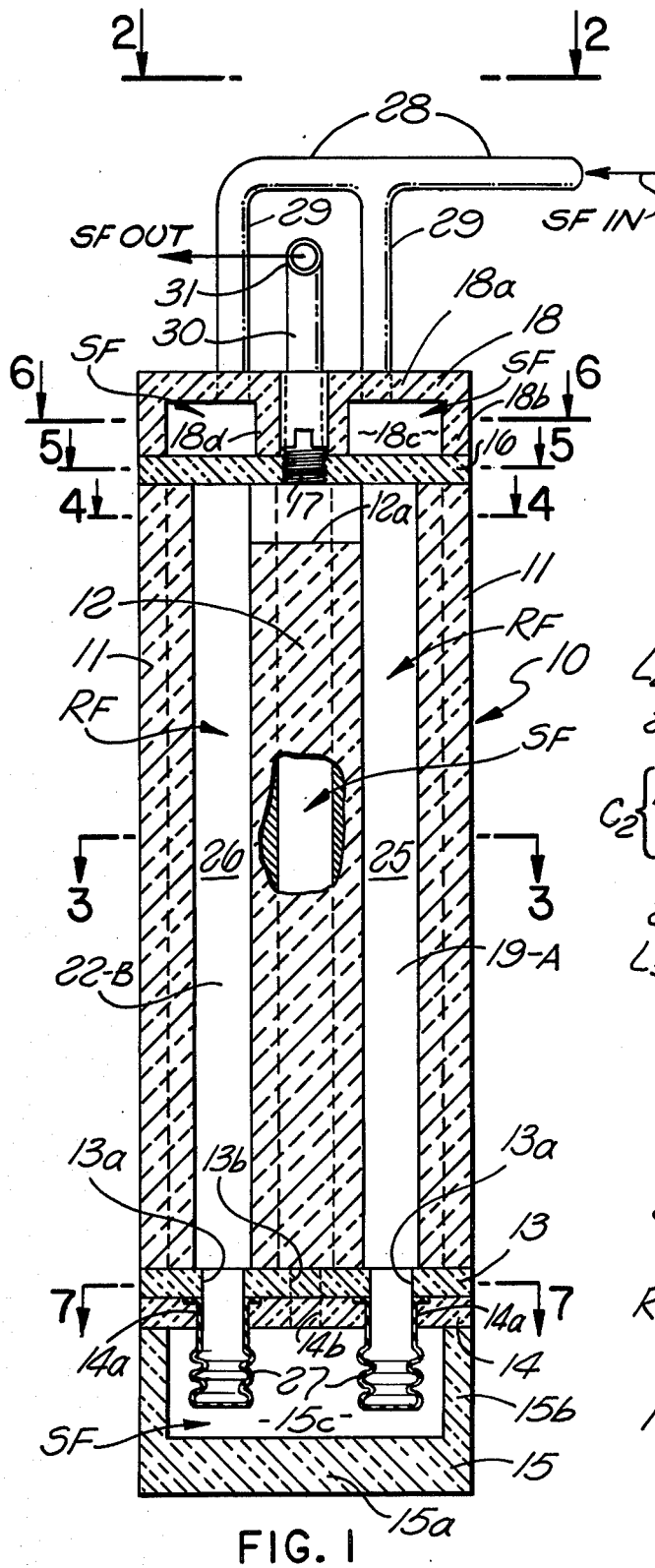
FIG. 1 is a sectioned elevation of the capacitive flowing fluid monitoring instrument of the present invention.
Figure 2:
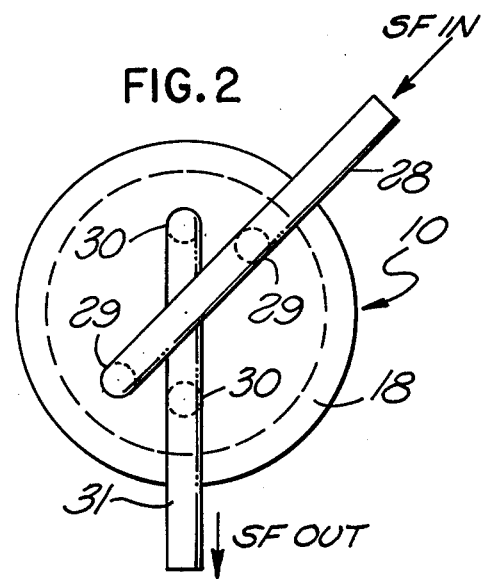
FIG. 2 is a top plan view of the monitoring instrument of FIG. 1.
Figure 5:
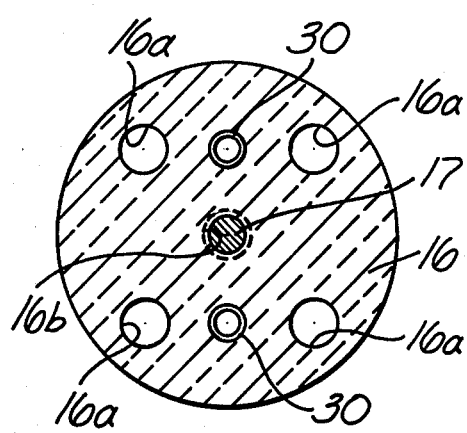
FIG. 5 is a cross-sectional view of the monitoring instrument of the invention taken at line 5—5 of FIG. 1.
Figure 6:
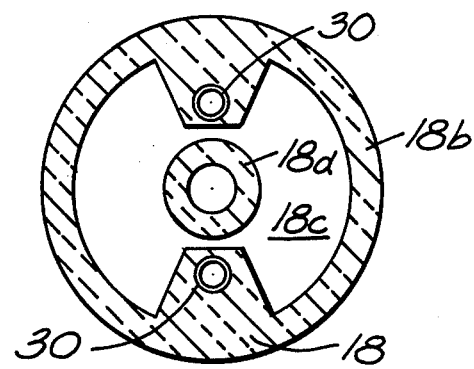
FIG. 6 is a cross-sectional view of the monitoring instrument of the invention taken at line 6—6 of FIG. 1.
Figure 7:
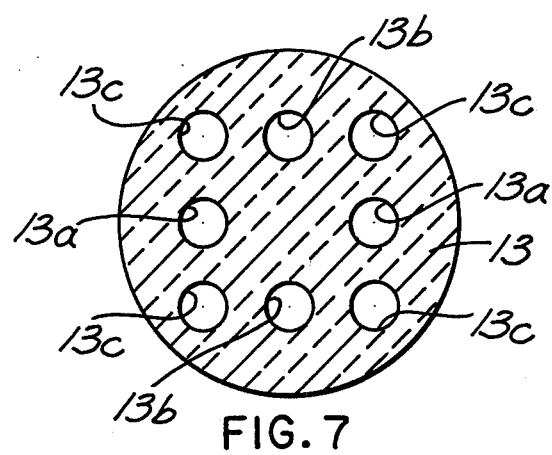
FIG. 7 is a cross-sectional view of the monitoring instrument of the invention taken at line 7—7 of FIG. 1.

Referring now to the drawings, a multi-capacitor flowing fluid monitoring instrument 10, in accordance with the present invention, is illustrated in FIG. 1. As shown, the monitoring instrument structure is comprised principally of a non-conducting casing 11 and central non-conducting capacitor element positioning member 12. The casing 11 is closed at its lower end by non-conducting header plates 13 and 14 and lower non-conducting header member 15 including bottom wall 15a and annular side wall 15b defining lower header chamber 15c. The upper end of casing 11 is closed by non-conducting header plate 16 (including plug 17) and non-conducting upper header member 18 including top wall 18a and annular side wall 18b defining upper header chamber 18c which surrounds a central annular wall 18d depending from header top wall 18a. FIGS. 5, 6 and 7 show, in cross-sectional views, the configurations of header plate 16, header member 18 and header plate 13, respectively.

Figure 3:
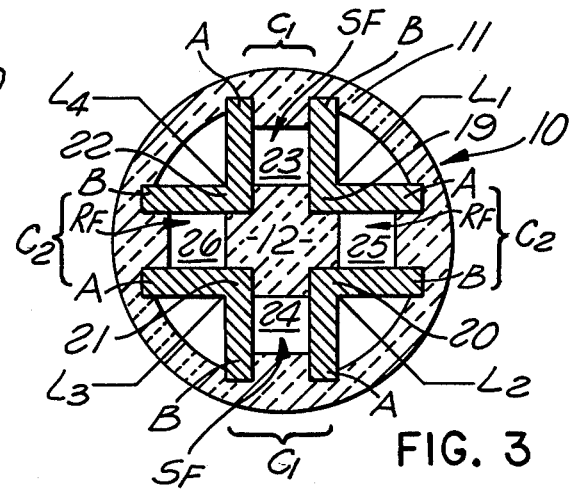
FIG. 3 is a cross-sectional view of the monitoring instrument of the invention taken at line 3—3 of FIG. 1.

Within the instrument casing 11, and as positioned and maintained by member 12, are four like electrically conductive capacitor elements 19, 20, 21 and 22 each comprised of two capacitive plates "A" and "B". The central positioning member 12 maintains the four capacitor elements in fixed spaced relationship from one another as shown in FIG. 3 and positions such elements so that each plate thereof defines with a plate of the next adjacent capacitor element a dielectric space therebetween whereby such elements together form four dielectric spaces 23, 24, 25 and 26. A reference fluid RF fills spaces 25 and 26. The reference fluid RF may be introduced to such spaces through hole 16b in header plate 16 and the channel defined at the upper end of positioning member 12 by wall 12a, side channel walls 12b and header plate 16. The dielectric spaces 25 and 26 communicate at their lower ends with holes 13a in header plate 13. Mounted between header plates 13 and 14 are pressure equalizing bellows 27 which depend from plate 14 into header chamber 15c and communicate through holes 13a with dielectric spaces 25 and 26.

Sample fluid SF is introduced to the monitoring instrument 10 through sample inlet line 28 and instrument inlet lines 29 which feed header chamber 18c. From the header chamber 18c the sample fluid is directed by header plate 16 through holes 16a downwardly through channels 11a, defined by the capacitor elements 19, 20, 21, and 22 and the instrument casing 11, for discharge through holes 13c of header plate 13 and matching holes in header plate 14 into lower header chamber 15c. From lower header chamber 15c the sample fluid passes upwardly through holes 14b and 13b in header plates 14 and 13, respectively, and thence through dielectric spaces 23 and 24 which communicate at their upper end, through header plate 16, with outlet lines 30 and sample discharge line 31.

As previously indicated, the flowing fluid monitoring instrument 10 of the invention includes four like electrically conductive capacitor elements each comprised of two capacitive plates "A" and "B". As shown in cross-sectional FIG. 3 two pairs of plate-type capacitors $C_1$ and $C_2$ are formed by the capacitor elements and their capacitive plates. Sample fluid SF fills the dielectric space 23 between plate B of element 19 and plate A of element 22 and the dielectric space 24 between plate A of element 20 and plate B of element 21. Thus, there is formed a pair of like plate-type capacitors $C_1$ of variable capacitance (impedance) value. The impedance value of capacitors $C_1$ varies in relationship to changes in the dielectric value of the sample fluid SF flowing through spaces 23 and 24.

Reference fluid RF fills the dielectric space 25 between plate A of element 19 and plate B of element 20 and the dielectric space 26 between plate A of element 21 and plate B of element 22. Thus, there is formed a pair of like plate-type capacitors $C_2$ of relatively fixed capacitance (impedance) value. Some small changes in the capacitance value of capacitors $C_2$ are possible since the dielectric value of the reference fluid RF filling spaces 25 and 26 is subject to small change due to changes in the temperature of such fluid which is positioned in indirect heat exchange relationship with sample fluid SF flowing in channels 11a. Thus, changes in the temperature of the sample fluid SF will result in like changes in the temperature of the reference fluid RF. Further, other small changes in the capacitance value of capacitors $C_2$ are possible since the dielectric value of the reference fluid RF filling spaces 25 and 26 is also subject to small change due to changes in the pressure imposed upon such fluid. Thus, changes in the pressure of thd sample fluid SF will be transmitted to the reference fluid RF through pressure equalizing bellows 27.

Figure 4:
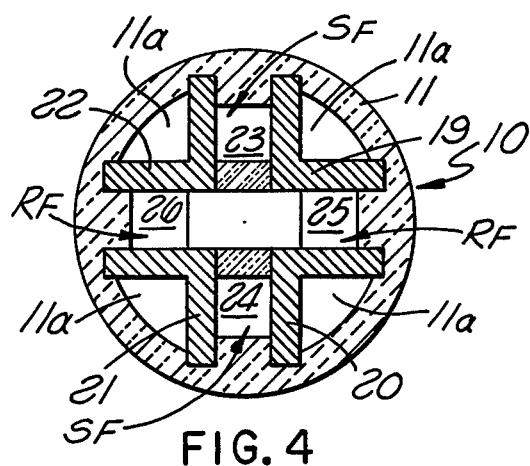
FIG. 4 is a cross-sectional view of the monitoring instrument of the invention taken at line 4—4 of FIG. 1.
Figure 8:
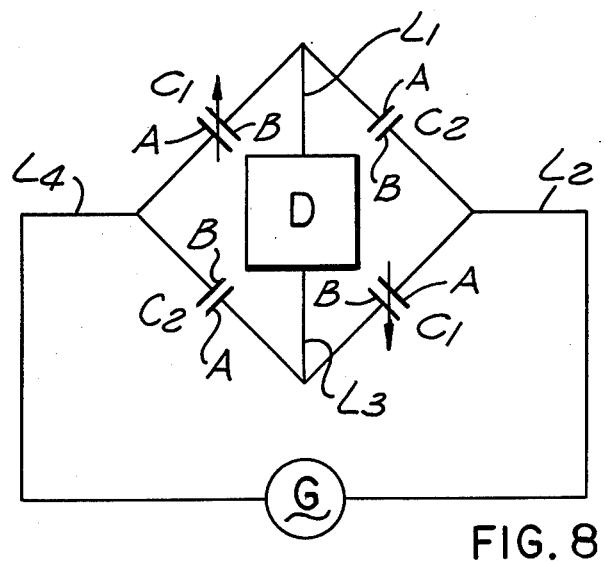
FIG. 8 is a schematic block diagram of circuitry in which the capacitors of the monitoring instrument of FIG. 1 are clearly identified in a classic Wheatstone bridge circuit configuration.

As will be appreciated from study of FIGS. 1, 3 and 4 of the drawings, the four capacitor elements 19, 20, 21 and 22 of the flowing fluid monitoring instrument of the invention are insulated from each other within the structure of the instrument and from the piping leading sample fluids into and out of the device. Electrically conductive lead wires L1, L2, L3 and L4 are connected, respectively, to the elements 19, 20, 21 and 22 (as shown in FIG. 3) and leave the instrument 10 via appropriate insulated passage therefrom. When these lead wires are further connected to alternating current generator circuitry "G" and detection, measurement and value indicating circuitry "D", as shown in FIG. 8, there results simple bridge circuitry of classic Wheatstone configuration.

The alternating current generator circuitry G is connected to the bridge circuitry (the $C_1$ pair of capacitors and $C_2$ pair of capacitors all contained in an intimate cluster within instrument casing 11) through screened input lead wires L2 and L4. Outlet wires (screened) L1 and L3 connect the bridge circuitry to the detector circuitry D (including appropriate current rectifier circuitry, if required), bridge interrogation circuitry, current measurement circuitry and current value indicating circuitry. Because all four capacitors of the bridge circuit are clustered together within the flowing fluid monitoring instrument the circuitry is not subject to stray capacitance and long leads may be used to connect the monitoring instrument with the current generator circuitry G or the detector, measurement and indicating circuitry D.

In applying the flowing fluid monitoring instrument of this invention to a flowing stream the desired reference fluid is first introduced to the instrument within channels 25 and 26 and sealed therein by closure plug 17. Identical calibrating fluid is then passed through the instrument via the sample inlet line 28 and removed therefrom via sample discharge line 31. During the passage of the calibrating fluid through the instrument the frequency and/or voltage of the applied alternating current and/or the detector circuitry (including its measuring and/or value indicating instrumentation) may be adjusted in known manner to give the appropriate sensitivity required for comparison of the density of the flowing fluid with the density of the reference fluid by the instrument.

For the bridge circuit of FIG. 8 the respective capacitors may have impedance values as indicated below:
Fixed value capacitors
$C_2$ impedance $=Z_2$
Variable value capacitors
$C_1$ impedance $=Z_1$ The detector circuitry D also presents an impedance value which may be designated as $Z_3$. The alternating current generator circuitry, at set frequency, has a constant voltage "e" which is applied across the bridge. Thus, If $Z_3$ is of small value, i.e., $Z_3 < Z_1$ and $Z_2$ then it can be established that the current "i" through the detector circuitry is:

$$i = (e\omega \div 2)(C_1 - C_2)$$

where
e is the voltage value and
$\omega = 2\pi$ frequency

The current value i in the detector circuitry changes in linear relation to changes in the capacitance value of capacitors $C_1$. Therefore, changes in the $C_1 - C_2$ relationship may be determined by measuring changes in the current value i. Furthermore, with appropriate detector and a.c. generator circuitry (e.g. by keeping the current i constant and varying the $\omega$ value) the readout of the $C_1 - C_2$ value can be effected by measuring the period of the angular frequency $\omega$. Thus, the readout instrumentation in the detector circuitry may yield digital values in direct linear relationship to the changes in capacitances $C_1$ and the dielectric value of the sample fluid (within the dielectric spaces 23 and 24) with respect to the dielectric value of the reference fluid.

From the foregoing, it will be appreciated that the bridge circuitry, comprised of the two like and substantially fixed value capacitors and the two like and variable value capacitors, is arranged to be in an unbalanced state (current flowing through the detection circuit) at all instances when the dielectric constant value of the sample fluid varies from the dielectric constant value of the reference fluid. With the bridge circuitry structured and operating in this fashion the detector circuitry reads the bridge unbalance (value of current flow) linearly as a direct measurement of dielectric constant value difference and the detector circuitry with associated measurement and value indicating circuitry will report or display such difference or may be modified by well known circuitry means to report or display the actual (changing) dielectric value of the sample fluid. Because of known relationships between dielectric constant value and density of fluids (as discussed hereinafter), the report or display of measured data may be as actual (changing) density value of the sample fluid, even if the fluid comprises a liquid/gas mixture or dispersion or a fluid comprised of different phases of the same substance.

It should be understood, that the multi-capacitor flowing fluid monitoring instrument of the invention is not limited to sensing characteristic changes in non-conducting fluids. It is equally practical to monitor the physical and chemical characteristics of conducting fluids, providing that the capacitor plates of the electrically conductive capacitor elements of the instrument are coated with an insulated film thereby preventing the passage of shorting components of current between such plates via the conducting fluids.

In applying the monitoring instrument to a flowing fluid stream, such as a petroleum products pipe line, sample inlet line 28 is connected by a suitable valved connection (not shown) to the products pipe line (not shown) so that a regulated sample stream can be withdrawn from such pipe line and passed into upper header chamber 18c, downwardly through channels 11a to lower header chamber 15c, upwardly through dielectric spaces 23 and 24, and outwardly of the instrument through outline lines 30 and sample discharge line 31. The sample fluids can be discharged from the instrument, by repressuring, into the products pipe line at a point downstream from the point from which they are withdrawn from such pipe line or they can be collected to permit further identification of the products to provide a correlation with dielectric constant measurement data generated by the monitoring instrument's circuitry.

Numerous examples can be suggested of flowing fluid streams which require monitoring for process or product control purposes and to which the method and instrumentation of this invention can be applied to measure and report fluid characteristics related to the dielectric constant value of the monitored fluid. Where the flowing fluid (liquid, liquid/liquid mixture or emulsion and liquid/solid mixture) is substantially incompressible the dielectric constant measurement is directly equatable to the density of the fluid and monitoring of the fluid via the method and instrumentation of the invention yields linear determination of density change. Where the flowing fluid is compressible (such as in the case of liquid/gas mixtures or dispersions or compressible liquids including liquid hydrogen) the same capacitive methodology and monitor structure of the invention is utilized with the detector circuitry calibrated to take into account the relationship between the dielectric constant of the material and its density found by Clausius and Mosotti. This relationship is $(\kappa-1) \div (\kappa+2) = \alpha\rho$, where "$\kappa$" is the dielectric constant, "$\alpha$" is the molecular polarizability constant for the particular material, and "$\rho$" is the absolute density of the material. Additionally, $\kappa = C_1/C_0$ where $C_0$ is the capacitance of a capacitor when there is a vacuum between the plates and $C_1$ is the capacitance when the fluid being measured is between the plates. Theoretically, this relation holds for all nonpolar materials regardless of phase.

As shown in the drawings, the casing 11, capacitive element positioning member 12, header plates 13, 14 and 16, and header members 15 and 18 of the monitoring instrument 10 are formed of non-conducting materials to provide an insulating supporting structure for the capacitor elements 19, 20, 21, and 22. The various members of the instrument structure are appropriately assembled with seals between such members where required to assure the separation of the reference and sample fluids and leak-free direction of the sample fluid through the instrument. The structural components of the instrument may be formed of electrically conducting material, such as stainless steel, provided the capacitor elements 19, 20, 21 and 22 are fully insulated from the structural components of the instrument.

While the invention has been described in detail with respect to a specific preferred structural embodiment and preferred method of operation, it will be understood by those skilled in the art that various changes and modifications may be made without departing from the spirit and scope of the novel concept of this invention. Therefore, it is intended by the appended claims to cover all such modifications and variations which fall within the true spirit and scope of the invention.

What is claimed is:

1. A method for comparing the dielectric properties of a flowing stream of fluid with the dielectric properties of a reference fluid which comprises:
    (a) providing a multi-capacitor flowing fluid sensor formed of a first pair of capacitors having like dielectric spaces within which a reference fluid is maintained under non-flow conditions as the dielectric material filling said spaces and a second pair of capacitors having like dielectric spaces within which a sample portion of the flowing stream of fluid is continuously passed as the dielectric material filling said spaces, said first pair of capacitors having substantially fixed and like capacitive value and said second pair of capacitors having variable capacitive value related to the variable dielectric constant value of said sample portion;
    (b) connecting the first and second pairs of capacitors of said sensor together to form the four capacitive sides of a Wheatstone bridge circuit, the pair of fixed value capacitors connected as two opposing sides of said bridge and the pair of variable value capacitors connected as the remaining two opposing sides of said bridge;
    (c) applying a source of alternating current of constant voltage and set frequency across said bridge circuit to a first set of bridge terminals at opposite corners of the bridge, each of said first terminals located between a fixed value capacitor and a variable value capacitor of said sensor;
    (d) interrogating the bridge circuit through a detection circuit connected across said bridge to a second set of bridge terminals independent of said first set of terminals and at opposite corners of the bridge, each of said second terminals located between a fixed value capacitor and a variable value capacitor of said sensor; and
    (e) measuring the current value in said detection circuit and indicating said value as a deviation value of dielectric constant of the sample portion of the flowing stream of fluid with respect to the dielectric constant of the reference fluid in direct linear relationship with said current value.

2. A method for comparing the dielectric properties of a flowing stream of fluid with the dielectric properties of a reference fluid as defined in claim 1 wherein the current value measured in said detection circuit is indicated as a deviation value of dielectric constant of the sample portion of the flowing stream of fluid with respect to the dielectric constant of the reference fluid and is expressed in direct relationship as a deviation of density of the sample fluid with respect to the reference fluid.

3. A method for comparing the dielectric properties of a flowing stream of fluid with the dielectric properties of a reference fluid as defined in claim 2 wherein the current value measured in said detection circuit is indicated as a deviation of density of the sample fluid with respect to the reference fluid in direct digital readout display.

4. A method for comparing the dielectric properties of a flowing stream of fluid with the dielectric properties of a reference fluid as defined in claim 2 wherein the current value measured in said detection circuit is indicated as a deviation of density of the sample fluid with respect to the reference fluid in direct analog display.

5. A method for comparing the dielectric properties of a flowing stream of fluid with the dielectric properties of a reference fluid as defined in claim 1 wherein the current value measured in said detection circuit is indicated in direct linear relationship with the dielectric constant value of the sample portion of the flowing stream of fluid.

6. A method for comparing the dielectric properties of a flowing stream of fluid with the dielectric properties of a reference fluid as defined in claim 5 wherein the current value measured in said detection circuit is indicated in direct relationship with the density value of the sample portion of the flowing stream of fluid.

7. A capacitive system for monitoring and comparing the dielectric properties of a flowing stream of fluid with respect to the dielectric properties of a reference fluid which comprises:
   (a) a multi-capacitor flowing fluid monitor-sensor formed of
      (i) a first pair of plate-type capacitors having like dielectric spaces,
      (ii) means for maintaining a reference fluid of known dielectric constant value under non-flow conditions within the dielectric spaces of said first pair of capacitors whereby said capacitors have substantially fixed and like capacitive value,
      (iii) a second pair of plate-type capacitors having like dielectric spaces, and
      (iv) means for continuously passing a sample portion of the flowing stream of fluid through the dielectric spaces of said second pair of capacitors whereby said capacitors have variable and like capacitive value related to the variable dielectric constant value of said sample portion;
   (b) means electrically connecting the first and second pairs of capacitors of said monitor-sensor together to form the four capacitive sides of a Wheatstone bridge circuit, the pair of fixed value capacitors connected as two opposing sides of said bridge and the pair of variable value capacitors connected as the remaining two opposing sides of said bridge;
   (c) a source of alternating current of constant voltage and set frequency connected across said bridge circuit to a first set of bridge terminals at opposite corners of the bridge, each of said first terminals located between a fixed value capacitor and a variable value capacitor of said monitor-sensor; and
   (d) a current detection circuit connected across the bridge to a second set of terminals independent of said first set of terminals and at opposite corners of the bridge, each of said second terminals located between a fixed value capacitor and a variable value capacitor of said monitor-sensor, said detection circuit including current value measurement and current value indication circuitry for expressing in direct linear relationship said current value as the dielectric constant value of the sample portion of the flowing stream of fluid.

8. A capacitive system for monitoring and comparing the dielectric properties of a flowing stream of fluid with respect to the dielectric properties of a reference fluid as claimed in claim 7 wherein the current detection circuit including current value measurement and current value indication circuitry expresses in direct relationship the density value of the sample portion of the flowing stream of fluid.

9. A capacitive system for monitoring and comparing the dielectric properties of a flowing stream of fluid with respect to the dielectric properties of a reference fluid as claimed in claims 7 or 8 wherein the first and second pairs of capacitors forming the multi-capacitor monitor-sensor of said system are coated with an insulating film.

10. A capacitive system for monitoring and comparing the dielectric properties of a flowing stream of fluid with respect to the dielectric properties of a reference fluid as claimed in claim 7 wherein the current value indication circuitry reports the dielectric constant value of the sample portion of the flowing stream of fluid in direct digital readout display.

11. A capacitive system for monitoring and comparing the dielectric properties of a flowing stream of fluid with respect to the dielectric properties of a reference fluid as claimed in claim 7 wherein the current value indication circuitry reports the dielectric constant value of the sample portion of the flowing stream of fluid in direct analog display.

12. A capacitive type monitoring instrument for comparing the dielectric properties of a flowing stream of fluid with respect to the dielectric properties of a reference fluid which comprises:
   (a) four electrically conductive capacitor elements each formed to present two electrically connected capacitive plates;
   (b) means for mounting said capacitor elements in fixed spaced relationship from one another and for positioning said elements so that each capacitive plate thereof defines with a capacitive plate of the next adjacent capacitor element a dielectric space therebetween whereby said mounted capacitor elements with their respective plates together form four plate-type capacitors;
   (c) means for maintaining a reference fluid of known dielectric constant value under non-flow conditions within the dielectric spaces of a first pair of said plate-type capacitors whereby said capacitors have substantially fixed and like electrical capacitance value;
   (d) means for continuously passing a sample portion of the flowing stream of fluid through the dielectric spaces of a second pair of said plate-type capacitors whereby said capacitors have variable and like electrical capacitance value;
   (e) means for electrically connecting the first and second pairs of capacitors of said monitoring instrument together to form the four capacitive sides of a Wheatstone bridge circuit, the pair of fixed value capacitors connected as two opposing sides of said bridge and the pair of variable value capacitors connected as the remaining two opposing sides of said bridge;
   (f) means for applying a source of alternating current of constant voltage and set frequency across said bridge circuit at a first set of bridge terminals at opposite corners of the bridge, each of said first terminals located between a fixed value capacitor and a variable value capacitor of said monitoring instrument; and
   (g) means for detecting and measuring current flow within the bridge circuit, said means being connected across said bridge circuit at a second set of bridge terminals independent of said first set of terminals and at opposite corners of the bridge, each of said second terminals located between a fixed value capacitor and a variable value capacitor of said monitoring instrument.

13. A capacitive type monitoring instrument for comparing the dielectric properties of a flowing stream of fluid with respect to the dielectric properties of a reference fluid as claimed in claim 12 wherein the four electrically conductive capacitor elements each consist of a rectangular metallic sheet folded along a line midway the edges thereof to form said electrically connected capacitive plates.

14. A capacitive type monitoring instrument for comparing the dielectric properties of a flowing stream of fluid with respect to the dielectric properties of a reference fluid as claimed in claim 12 wherein the four electrically conductive capacitor elements each consists of an elongated metallic sheet folded 90° along a line midway the edges thereof to form said electrically connected capacitive plates.

15. A capacitive type monitoring instrument for comparing the dielectric properties of a flowing stream of fluid with respect to the dielectric properties of a reference fluid as claimed in claim 12 wherein the four electrically conductive capacitor elements are coated with an insulating film.

16. A capacitive type monitoring instrument for comparing the dielectric properties of a flowing stream of fluid with respect to the dielectric properties of a reference fluid as claimed in claim 12 wherein means are provided for equalizing the pressure of the reference fluid with respect to the pressure of the sample portion of the flowing stream of fluid.

17. A capacitive type monitoring instrument for comparing the dielectric properties of a flowing stream of fluid with respect to the dielectric properties of a reference fluid as claimed in claim 16 wherein the means for equalizing the pressure of the reference fluid with respect to the pressure of the sample portion of the flowing stream comprises bellow means in communication with said reference fluid and in pressure interfacing relationship with said sample portion of fluid.

18. A capacitive type monitoring instrument for comparing the dielectric properties of a flowing stream of fluid with respect to the dielectric properties of a reference fluid as claimed in claim 12 wherein means are provided for equalizing the temperature of the reference fluid with respect to the temperature of the sample portion of the flowing stream of fluid.

19. A capacitive type monitoring instrument for comparing the dielectric properties of a flowing stream of fluid with respect to the dielectric properties of a reference fluid as claimed in claim 18 wherein the means for equalizing the temperature of the reference fluid with respect to the temperature of the sample portion of the flowing stream comprises means for directing said sample portion of fluid in indirect heat exchange relationship to said reference fluid.

* * * * *